(12) United States Patent
Lell (10) Patent No.: US 10,561,794 B2
(45) Date of Patent: Feb. 18, 2020

(54) NEEDLE-FREE INJECTION DEVICE COMPRISING A MEMBRANE

(71) Applicant: Peter Lell, Moosburg (DE)

(72) Inventor: Peter Lell, Moosburg (DE)

(73) Assignee: Peter Lell, Moosburg (DE)

( * ) Notice: Subject to any disclaimer, the term of this patent is extended or adjusted under 35 U.S.C. 154(b) by 383 days.

(21) Appl. No.: 15/500,955

(22) PCT Filed: Aug. 3, 2015

(86) PCT No.: PCT/EP2015/067838
§ 371 (c)(1),
(2) Date: Feb. 1, 2017

(87) PCT Pub. No.: WO2016/020330
PCT Pub. Date: Feb. 11, 2016

(65) Prior Publication Data
US 2017/0216530 A1    Aug. 3, 2017

(30) Foreign Application Priority Data
Aug. 2, 2014    (EP) ..................................... 14179613

(51) Int. Cl.
*A61M 5/30*    (2006.01)
(52) U.S. Cl.
CPC ...... *A61M 5/3015* (2013.01); *A61M 2202/064* (2013.01); *A61M 2205/7545* (2013.01); *A61M 2205/8206* (2013.01)
(58) Field of Classification Search
CPC .................................................. A61M 5/3015
See application file for complete search history.

(56) References Cited

U.S. PATENT DOCUMENTS

| 3,308,818 | A   |   | 3/1967 | Rutkowski |
|-----------|-----|---|--------|-----------|
| 5,399,163 | A   |   | 3/1995 | Peterson et al. |
| 6,258,063 | B1  | * | 7/2001 | Haar ................... A61M 5/2425 604/141 |
| 7,160,265 | B2  |   | 1/2007 | Lell |

(Continued)

FOREIGN PATENT DOCUMENTS

| CA |      2423647 A1 | 4/2002 |
|----|-----------------|--------|
| DE | 102007004211 A1 | 7/2008 |

(Continued)

OTHER PUBLICATIONS

International Search Report for PCT/EP2015/067838 dated Nov. 5, 2015.

(Continued)

*Primary Examiner* — Nathan R Price
*Assistant Examiner* — Dung T Ulsh
(74) *Attorney, Agent, or Firm* — Drinker Biddle & Reath LLP (57) ABSTRACT

The invention relates to a needleless injection device, containing at least one membrane, or a corresponding device for needleless injection of a substance, having at least one membrane, with which a powdered, gel-like or liquid agent, in particular an active agent, can be injected in a needleless manner into a tissue or a body by means of high impact speed. The invention also relates to a method for such a needleless injection device containing a membrane, and use thereof.

12 Claims, 4 Drawing Sheets

(56) References Cited

U.S. PATENT DOCUMENTS

| | | |
|---|---|---|
| 8,262,604 B2 | 9/2012 | Asmussen et al. |
| 2003/0114789 A1* | 6/2003 | Haar ................... A61M 5/30 |
| | | 604/69 |
| 2005/0214227 A1* | 9/2005 | Prestrelski ........... A61K 9/0021 |
| | | 424/46 |
| 2007/0038175 A1 | 2/2007 | Van Laar |
| 2010/0179473 A1* | 7/2010 | Genosar ............ A61M 5/14248 |
| | | 604/70 |
| 2012/0253270 A1* | 10/2012 | Steinbach ............ A61K 9/0024 |
| | | 604/67 |

FOREIGN PATENT DOCUMENTS

| | | |
|---|---|---|
| EP | 1557190 A1 | 7/2005 |
| EP | 2514477 A1 | 10/2012 |
| WO | WO-9620022 A1 | 7/1996 |
| WO | WO-9831409 A2 | 7/1998 |
| WO | WO-0043058 A1 | 7/2000 |
| WO | WO-0054827 A1 | 9/2000 |
| WO | WO-2004071558 A1 | 8/2004 |

OTHER PUBLICATIONS

Written Opinion of the International Searching Authority for PCT/EP2015/067838 dated Nov. 5, 2015.

* cited by examiner

NEEDLE-FREE INJECTION DEVICE COMPRISING A MEMBRANE

CROSS-REFERENCE TO RELATED APPLICATIONS

This application is a national stage application (under 35 U.S.C. § 371) of PCT/EP2015/067838, filed Aug. 3, 2015, which claims benefit of European Application No. 14179613.6, filed Aug. 2, 2014, both of which are incorporated herein by reference in their entirety.

The invention relates to a needleless injection device, containing at least one membrane, or a corresponding device for needleless injection of a substance, having at least one membrane, with which a powdered, gel-like, or liquid agent, in particular an active agent, can be injected in a needleless manner into a tissue or a body by means of high impact speed. The invention also relates to a method for such a needleless injection device containing a membrane, and use thereof.

A successful injection lies in the fact that sufficient substance is introduced into the body through the tissue barrier or body barrier, in particular such as the skin of humans or animals. The basic principle of injecting an agent in a needleless manner by means of high pressure has been known for some time (for example see U.S. Pat. No. 3,308,818).

Various types of needleless injection devices are described in the prior art, for example (not exhaustively) a cylinder-piston unit comprising a pretensioned spring element (DE 10 2007 004 211 A1) or by means of what are known as injection cartridges (WO 98/31409) and by means of a gas cartridge for acting on a piston (U.S. Pat. No. 5,399,163).

Furthermore, needleless injection devices can consist of a pyrotechnic drive, which for example is used to actuate a piston and in this way causes an active agent to be pressed out from a cannula (EP 1 557 190 A1).

A further embodiment of a needleless injection device lies in a pyrotechnic approach, in which case an explosion is generated in a chamber (also referred to as a firing chamber), wherein the released energy is used to transfer a pulse to a membrane, whereby a substance adsorbed by the membrane is sufficiently accelerated and detaches from the membrane in the direction of the tissue.

A device of this type is disclosed in WO 2004/071558 A1. However, a generic embodiment of this type can still be improved, such that a desired substance can be introduced into a body in an improved manner.

The present invention therefore makes reference to a generic embodiment according to WO 2004/071558, but addresses the objective problem of improving the needle-free injection.

The invention therefore relates to a needleless injection device comprising a skin-side membrane (15), which can also be described hereinafter as a double or multiple membrane, wherein the membrane (15) is provided with a particle application (25) on the skin-side membrane (15), wherein at least some of the particles are larger than the rest of the particles, it also being preferred if at least some of the particles are at least 2 times, 5 times, 10 times, or 20 times larger than the rest of the particles.

In a further embodiment it is preferred that at least one or more larger particles are contained in the totality of the particle application (25) in addition to smaller particles. The proportion of the larger particles in the totality of the particle application can also be 1%, 5%, 10% and more.

Within the scope of this invention the term "particles" is understood to mean for example dust, grains, crystals, powders or small solid particles, for example (not exhaustively) sugar, glass, plastic or metal particles, but also gel and liquid particles, which can measure from approximately 1 nm to 1,000 µm in size. These gel or liquid particles can be created from a gel or liquid film on the membrane as a result of the sudden acceleration and braking thereof during the detachment of the gel or liquid.

By way of example, such particles can consist of pharmaceutically acceptable or safe materials, such as those which can be easily broken down by the body, for example sugar (glucose, etc.). It is key that a particle application (25) exists, i.e. a membrane (15) is dusted with particles or is coated with a gel or liquid layer. Such techniques are known appropriately to a person skilled in the art. Furthermore, the particles can also consist of a pure substance or can be a substance mixture. By way of example, the particles can contain an active agent or can consist completely of an active agent.

Is now essential to the invention that one or more larger particles are present in the particle application in addition to smaller particles, wherein the object of one or more larger particles is to penetrate the skin or the body by creating an opening, to penetrate as deeply as desired, and in this way to advantageously create an active area to be dusted that penetrates accordingly deeply into the skin or the body for the subsequent smaller particles, and thus advantageously facilitate the penetration and infiltration of the smaller particles Without the use of at least one or more larger particles, the smaller particles cannot infiltrate the skin tissue or the body sufficiently deeply at the impact speed available by means of the applicator/membrane device. The desired infiltration depth is advantageously set by the properties of the larger particles. What are decisive are the impact speed defined by the membrane device, the size and mass of said larger particles, which serve as openers so to speak, rising with the cube of the radius and the specific density of the agent, and also the geometry of said larger particles at the moment of impact against the skin or the body surface.

Tubular and capillary-like openings as well as a penetration cone (or supersonic cone) are advantageously and surprisingly obtained in the skin as a result of the larger particles, such that on the one hand the surface is enlarged and on the other hand capillary forces can be used. These tubular and capillary-like openings can be used advantageously by the relatively smaller particles.

A further key advantage of the invention lies in the fact that the skin is bombarded by the larger particles, which for example are very quick (up to 650 m/s) and penetrate deep into the skin, with a penetration time of approximately only 10 to 50 microseconds, and consequently the individual or the animal no longer perceives this deep penetration as pain, although the penetration area or the bombarded area can be very large and very many pain receptors are encountered or stimulated during the impact.

Compared to the prior art, and more specifically all liquid needleless injection methods, analgesia can be achieved only if the injection channel has a very small diameter of at most 0.15 mm and consequently cannot be detected by the pain receptors of the skin.

Within the scope of this invention, "particle application (25)" means particles that contain at least one agent or active agent and for example are fixed to the outer (skin-side) membrane (15) using oils, amongst other things, or adhere to said membrane by adhesion, i.e. are retained on the membrane. By way of example, the applied particles can contain means which allow a drying of the particles on said membrane. In particular, additional adhesion promoters or additives are suitable and added, such as oils or other preferably pharmaceutically suitable auxiliaries and additives.

A space devoid of air is disposed between the particle application (25) and the skin.

A particle application (25) is also understood to mean gel and liquid particles which can measure from 1 nm to 1,000 μm in size. These gel or liquid particles can be created from a gel or liquid film on the membrane as a result of the sudden acceleration and braking thereof as the gel or the liquid detaches.

The term "particles containing or consisting of an agent" includes all and any agents, substances, materials, or media.

By way of example, the larger particles can have a size of 1, 10, 20, 40 to 1,000 μm, whereas the smaller particles are 1 to 1,000 μm large (for example what are known as sub-micron particles), which also can never penetrate the skin, for example at an impact speed of 650 m/s. By way of example, the larger particles can contain glass, plastic or metal beads as opener, or can be predominantly sugar crystals in the case of injection into the skin, so as to then be able to break down these particles again, whereas the smaller particles contain an active agent. Of course, a person skilled in the art is able to select suitable other relations of small to large particles.

The invention therefore also relates to a particle application (25), wherein the particles consist of two or more different agents and the larger particles do not contain any active agent and the smaller particles contain an active agent. For example, the larger particles can consist of sugar and the smaller particles can consist of the active agent as such, for example in a crystalline or powdered form, or in the form of nanoparticles or liposomes containing an active agent.

Even with a flight path of at least 5 mm, in particular 5 to 10 mm, a sufficient effect is attained, as demonstrated in the following examples and drawings. This will be explained in greater detail further below with the distancing according to the invention.

In accordance with the invention, there is a sufficient pulse transfer to a membrane (15), which can also be formed as a double membrane or multi-layered membrane, such that the particles are sufficiently accelerated, more specifically preferably to speeds of 600 m/s and more.

Within the scope of this invention, the term "pulse (transfer)" is therefore also understood to be synonymous with a transfer or application of force or pressure which in any case is sufficient to accelerate and detach the particle application (25) applied to the skin-side membrane (15) at the desired high speeds, whereby the particles initially fly freely in the direction of the tissue or skin (18) or body so as to strike there, break through the tissue barrier or body barrier, and infiltrate to the desired depth of the tissue, in particular the skin or the body. The flying particles over the flight path can be described as a particle jet, wherein the particles can clump together to form particle clusters.

Within the scope of this invention, "skin" means a tissue barrier of a human, mammal or animal. The skin, as the largest organ of the human body, performs numerous vital functions, and in particular the epidermis serves as a barrier organ. This barrier function is maintained, inter alia, by skin lipids. These epidermal lipids, such as glycosphingolipids, ceramides, sterols, and sterol esters, fatty acids, triglycerides, n-alkanes, or various polar lipids, are released in the keratinisation process. Due to the needleless or needle-free application according to the invention, these substances consequently can enter the body locally and can lead into the bloodstream as appropriate.

The necessary activation energy for pulse (transfer) can therefore be provided by means of an activation unit, more specifically by means of impact or preferably explosion or destination, in particular (not exhaustively) a detonator (10), igniter, firing pin or igniting pin, more specifically via a trigger mechanism by means of friction, impact or suitable power supply.

The necessary activation energy for the pulse (transfer) can therefore be provided by means of an activation unit, more specifically by means of impact or preferably explosion or detonation, in particular (not exhaustively) a detonator (10), igniter, firing pin, or ignition piece, more specifically via a triggering mechanism by means of friction, impact or suitable power supply.

Figure 1:
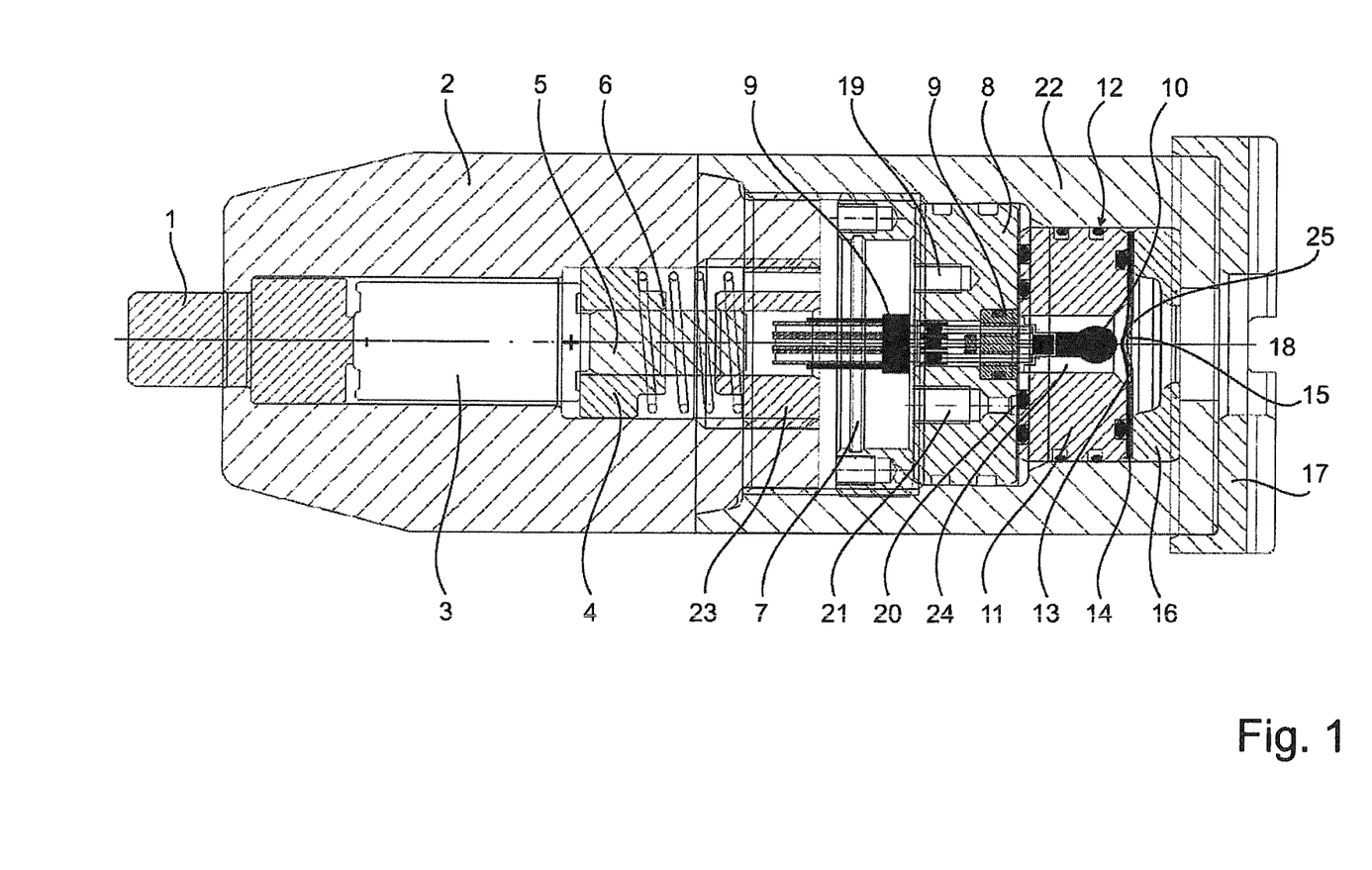
FIG. 1 shows a cross-section of the injection device according to the invention with fixed membrane.

A suitable activation unit is illustrated in FIG. 1 by way of example. The battery (3) is pressed against a contact spring (6) and against a contact pin (5) by means of a trigger or button (1), thereby closing the electrical circuit via the connections (9) and the EED (10), consequently igniting the EED (10). Alternative triggering mechanisms are known to a person skilled in the art (friction wire, jumper wire, clicker mechanism beating against impact-sensitive ignition mixture, etc.).

In a further preferred embodiment said activation unit (1, 2, 3, 4, 5, 6, 7, 8, 9, 10) is oriented in the axial direction relative to the chamber (11) inclusive of combustion chamber (24), and opposite the membrane (15).

The membrane (15) according to the invention can be fixed or movable or displaceable and can also be formed as a double membrane (13, 15) or multi-layered membrane, and consequently such a membrane in accordance with the invention is the recipient of such a pulse transfer, such that a corresponding particle beam (see above) can be created.

In a preferred embodiment, the membrane (15) according to the invention consists of metal or a material of corresponding hardness and ductility, such as steel, plastics, but particularly preferably titanium or sheet titanium. In particular, titanium has an advantageous high formability limit with very good capability of acceleration due to its lower specific density compared with steel, whereby, with relatively low pressures in the firing chamber, a much quicker speed of the membrane surface or of the buckling membrane is achieved. Here, what is key is the acceleration index AI=yield point $\text{sigma}_{0.2}$/density ro.

Instead of a single membrane, a double membrane can also be provided, i.e. for example instead of a single membrane 1 mm thick, two membranes each 0.5 mm thick are placed one over the other so as to form a double membrane. Other thickness ratios are also possible, for example 0.6 mm in the direction of the chamber and 0.4 mm in the direction of the skin.

A multi-layered membrane is provided in accordance with the invention when more than 2 layers are placed above one another. By way of example, a sealing layer close to the edge or an insulating layer can be introduced between the double membrane in order to modify the speed distribution of the detaching particles.

In the case of a fixed double membrane (13, 15), both membranes—the double membrane—are attached/fixed with a support disc (16), in particular to the chamber (11) and consequently are immovable in the edge region. It is also preferred that the inwardly directed membrane (13) on the firing chamber side has a thickness of from 0.1 mm to 0.6 mm, preferably 0.2 mm to 0.6 mm, particularly preferably 0.5 mm. The outwardly directed skin-side membrane (15) preferably likewise has a thickness of from 0.1 mm to 0.6 mm, preferably 0.2 mm to 0.6 mm, particularly preferably 0.5 mm. The membranes (13, 15) can contact one another wholly or partially.

In a further preferred embodiment, however, the inner membrane (13) has a distance from the skin-side membrane (15), more specifically preferably of from 0.2 mm to 1.5 mm, particularly preferably 1 mm. The necessary spacing can be provided by means of a spacer (14) between the two membranes. This measure causes an efficient prevention of the bursting of the skin-side membrane.

In a further preferred embodiment, the present invention relates to a needleless injection device comprising a (firing) chamber (11) containing a pyrotechnic material, wherein the chamber (11) has at least one membrane (15) at a discharge opening, wherein the membrane (15) is provided towards the skin side with a particle application (25). The membrane (15) leads to the firing chamber (11) and combustion chamber (24) thereof. In the case of a double membrane (13, 15) or multiple membrane, the membrane (13) leads to the firing chamber (11) and combustion chamber (24) thereof.

In a further particularly preferred embodiment, the membrane (15) or double membrane (13, 15) is completely or partially curved towards the chamber (11) and into the combustion chamber (24) thereof, over the entire area or preferably in the central radial region about a circle midpoint. Such a concave curvature of the membranes from the viewpoint of the firing chamber can be achieved by a person skilled in the art by means of known methods. Said curvature of the membrane (13) or double membrane (13, 15) according to the invention additionally allows an advantageous increased speed of from 10 to 15%, together with focussing and acceleration of the applied substances (25) in the direction of the skin (18)—presumably by shock wave focussing.

In a further preferred embodiment, the two membranes (13, 15) have support discs (16). The support discs are preferably made of plastic, brass, etc., which is particularly suitable for energy absorption. In addition, the support disc is adapted in terms of energy, preferably with a tapering towards to the skin (18).

At the same time, the support disc (16) can be thinly coated on its inner contour with a soft plastic, for example with polyethylene, so as to advantageously significantly reduce the triggering noise of the device—for example the snap-like noise created when a metal membrane impacts on a metal support disc is avoided.

A fundamental and generic construction of a needleless injection device with fixed membrane is shown for example in FIG. 1 together with a key, wherein, for the function of the injection device according to the invention, the housing (22) and also the parts (7) to (16) should be taken into consideration. Here, the parts (7) to (16) can be installed readily in a differently formed housing (22), and a detonator, in particular an EED (10), can also be supplied differently with energy, without modifying the function of the parts or the device. Specific embodiments will be described in greater detail.

Figure 2:
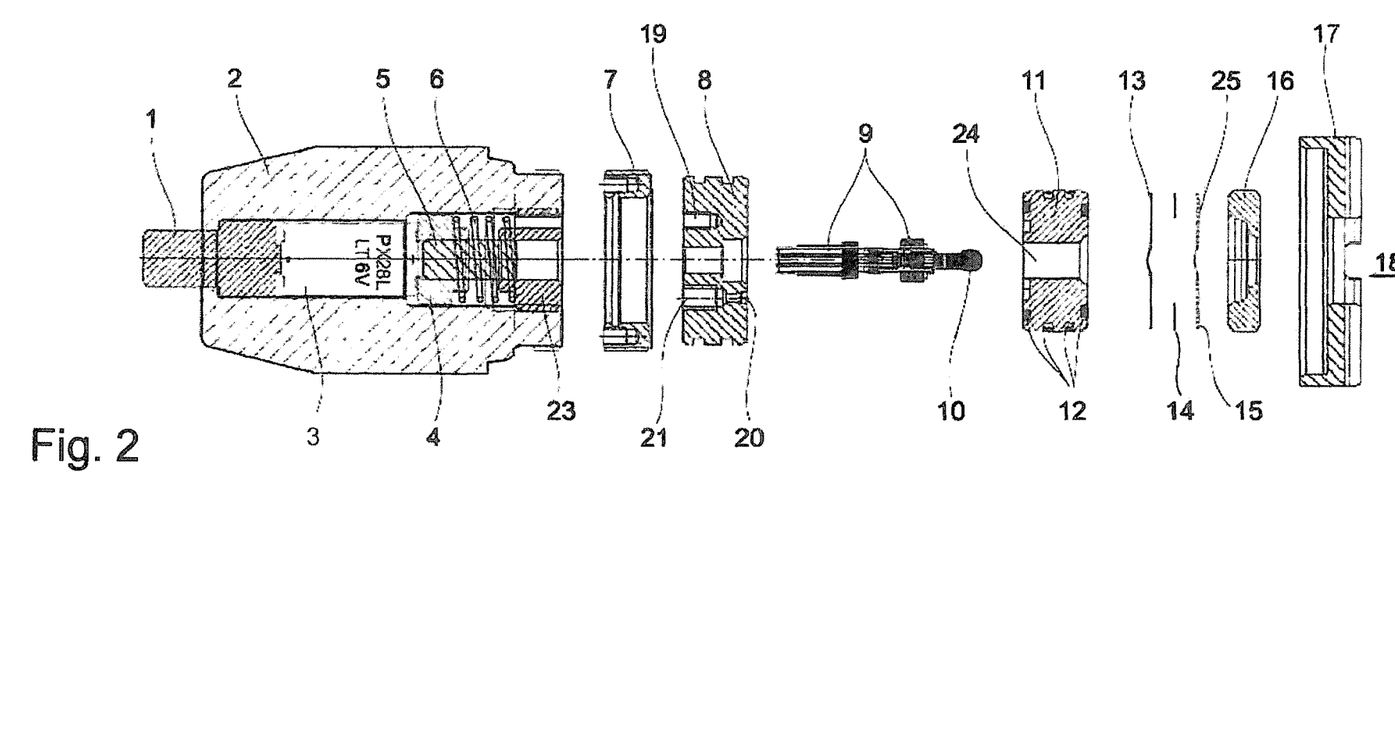
FIG. 2 shows more clearly the parts for producing the injection device according to the invention with fixed membrane.

The geometry of the individual parts in FIG. 1 can be modified or integrally combined in part depending on the requirements. By way of example, parts (7) to (9) can be integrally combined to form one part, or the part (7) can be omitted, for example if part (8) has an external thread and is screwed into the housing (22) (or for example is held in the housing (22) by retaining ring) or is an insertion part in the injection mould of the housing (22) (see also FIG. 2). The parts (1) and also the parts (4) to (6) and (23) can also be omitted by the use of a conventional button to place the detonator (EED) (10) in electrical contact with the battery (3).

It is also preferred in accordance with the invention that the needle-free device has a chamber containing a pyrotechnic material, such that a pulse transfer can be provided by means of explosion or destination.

Within the scope of this invention, a "pyrotechnic material" is understood to mean any material which can be made to explode using activation energy. These materials for example can be solid or gaseous substances, such as azides, tetrazene, nitrocellulose, picric acid, etc. or other pyrotechnic materials known to a person skilled in the art. It is essential to the invention that the explosion energy should allow a sufficient pulse transfer to the membrane (15) according to the invention, such that the particle application (25) can be brought to high speeds, and ultimately the particles can be detached.

The pyrotechnic material is contained in accordance with the invention in a chamber (11) that is fully closed outwardly, more specifically in the combustion chamber (24), preferably in the form of a detonator (10), in particular in the form of a mini detonator (EED) (10). In addition, further pyrotechnic material can also be introduced.

In a further embodiment, the combustion chamber (24) in the chamber (11) can be provided preferably with a viscous, thick mass, such as fat, oils and the like, for the purpose of reducing the size of the empty space in the combustion chamber (24), thus increasing the pressure rise in the event of a small charge of the detonator (EED) (10) and at the same time creating an optimal coupling of the shock or pressure wave starting from the detonator to the membrane.

The chamber (11) preferably has O-rings for sealing (12). Furthermore, the chamber (11) can have a vent (20) inclusive of associated cover (21).

In a further preferred embodiment the injection device contains an attachment (17) and/or support disc (16), such that a defined distance, for example of approximately 5-10 mm, is achieved between the skin (18) and the membrane (15) (see above), in order to hold any buckling membrane reliably away from the skin or surface of the body and to obtain a defined flight path, wherein the membrane is preferably distanced parallel to the skin. This aforementioned distancing allows a sufficient protrusion of the accelerated larger particles compared to the smaller particles from a particle application (25) on a membrane (15).

The aforementioned embodiments therefore advantageously allow the introduction or penetration of the particles, more specifically of the smaller particles, into the skin or a body, more specifically through openings which have been caused by one or more larger, quicker particles prior to the smaller particles reaching the skin or inside the body after impact. As a result of the embodiment of the device with membrane or of the applicator with membrane, it is also advantageously possible that the particles applied to the membrane experience an optimised pulse transfer or acceleration to very high speeds and with formation of a particle jet up to 800 m/s.

The invention also relates to the use or application of one or more agents, in particular active agents, in particular a drug for needle-free application by means of the injection device according to the invention in accordance with one of the above embodiments.

The invention also relates to the use or application of agents, in particular agents having any function and suitability, such as dyes or lubricants or materials having other specific properties for needleless insertion into or below the surfaces or body of technical objects by means of the injection device according to the invention in accordance with one of the above embodiments.

The invention therefore relates to an injection device according to any one of the above embodiments for use of an agent or an active agent, in particular a drug, for needle-free application.

The following examples, and drawings are intended to explain the invention in greater detail, but without limiting the invention thereto.

FIG. 3:

Image sequence, left column:

Shooting of approximately 10 glass beads 250μ in size, which are used as penetration bodies, at approximately 650 m/s into a skin-like gel. In the first image at the top, it is already possible to see the structure of the impact cone in the gel (slanted pressure shock), which can intensify or build further so as to then leave a relatively thin, air-filled strand/tube over the particular penetration body (bottom image).

Image sequence, right column:

Shooting of 5 glass beads (particles) 500μ in size, which are used as penetration bodies, at approximately 650 m/s into a skin-like gel. The structure of the impact cone in the gel (slanted pressure shock) can already be seen in the first image at the top and can then intensify so as to then leave a relatively thin, air-filled strand/tube over the particular penetration body (bottom image, the strands are slightly inflated here).

FIG. 4:

Image sequence top left=2 images, approximately 50 glass beads (particles) having a diameter of 500 μm are shot into artificial skin, dusted on the membrane with sugar particles measuring 20 to 80 μm in size, which are coloured black.

Image sequence lower left=2 images, approximately 100 glass beads 250 μm in size, dusted on the membrane with sugar particles 20 to 80 μm in size, which are coloured black.

Image sequence right=4 images, ditto for glass beads/penetration bodies 500 μm in size.

Figure 3:
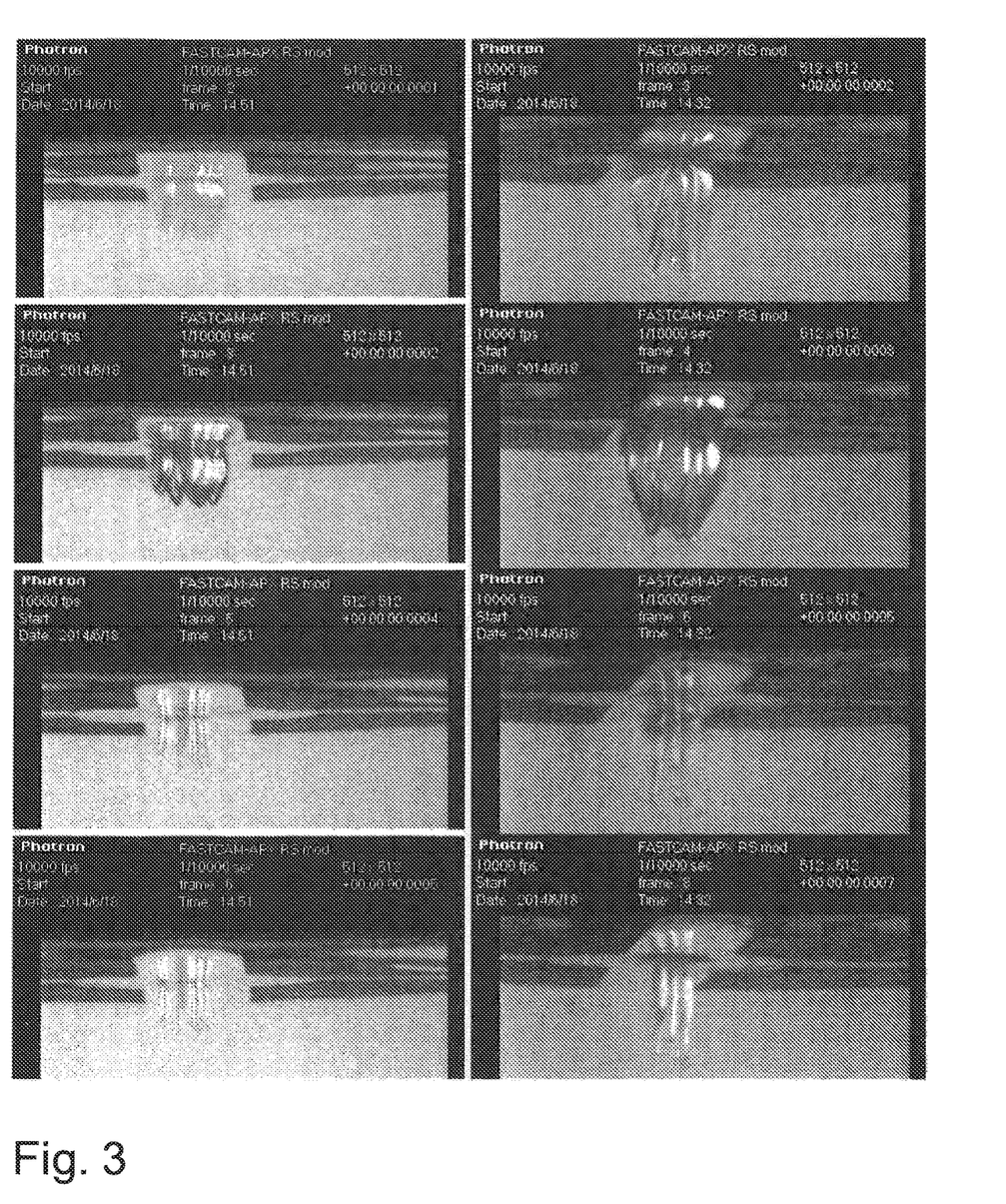
Figure 4:
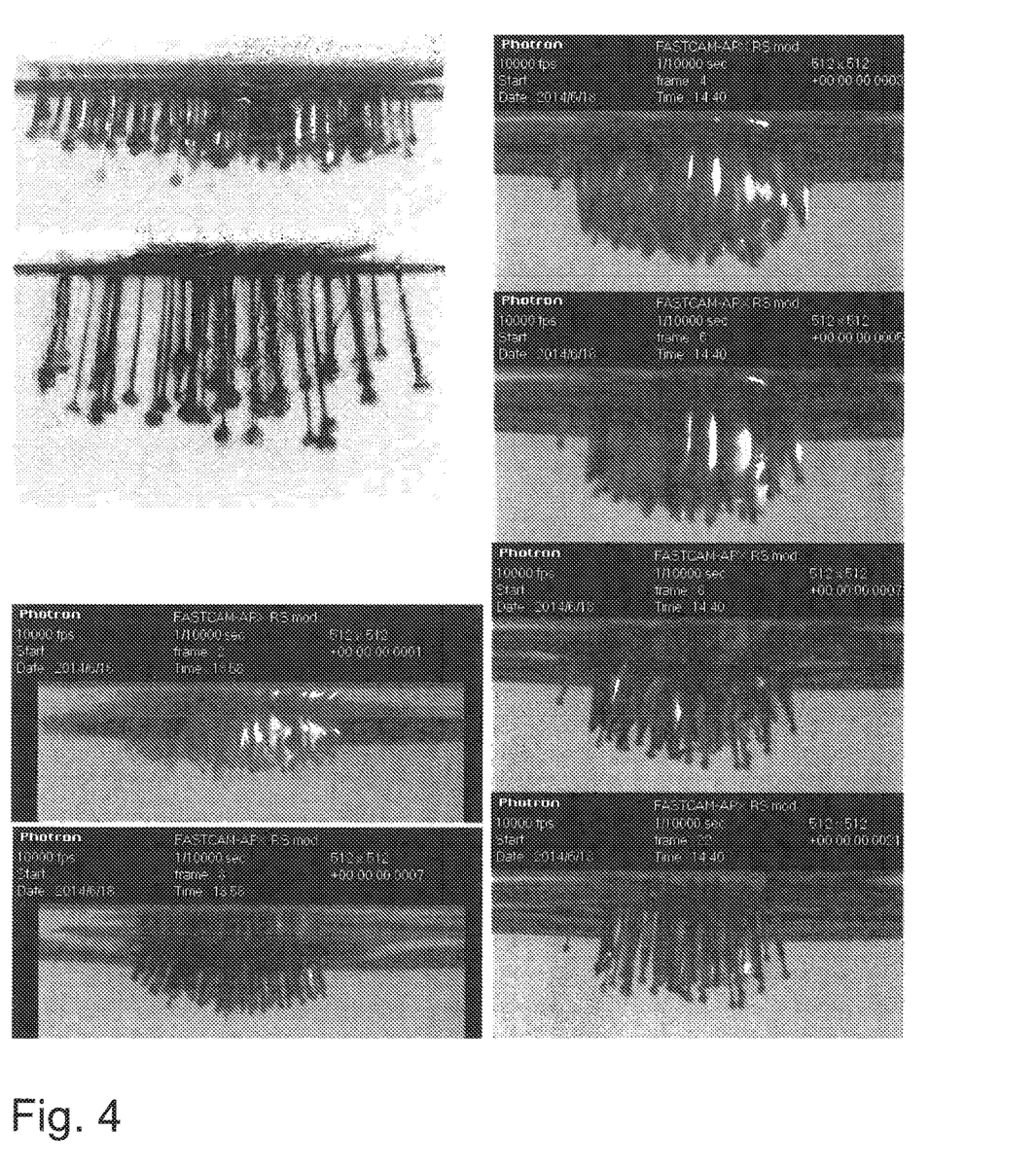

Each of the above 3 image sequences shows the situation after triggering the needle-free injector or the pyrotechnic membrane device when, at the same time, small particles are also applied to/sputtered on the skin-side membrane of the penetration bodies. The penetration bodies here firstly penetrate at approximately 650 m/s, then an impact cone forms over each penetration body, which form a large inner surface for the somewhat slower particles flying in subsequently at approximately 620 m/s. Shortly thereafter, the impact cones "smack" together again (the speed of the penetration bodies is in the meantime below the speed of sound of the material of the penetrated body/the skin/the gel or has dropped to 0 m/s) and compact the previously introduced particles so to speak, which are hereby trapped as it were.

When sugar particles are used as penetration bodies, for example for medical purposes, they are broken down by the body/skin/tissue after their administration, and after this the particles compacted in the "tubes" created by the sugar particles remain.

KEY 1 trigger, button
2 trigger housing
3 battery
4 spring cap
5 contact pin
6 contact spring
7 grooved nut
8 holder for glass feedthrough
9 glass feedthrough with connections
10 mini detonator or ignition piece, EED
11 firing chamber or chamber
12 O-ring seal of the firing chamber (can also be omitted in some embodiments of the device)
13 inner membrane
14 spacer, also performs sealing functions
15 skin-side membrane, fixed to membrane (13) and spacer (14)
16 support disc
17 attachment
18 skin or the surface to be penetrated (bears against 17, not shown)
19 thread for ground connection screw (can also be omitted in some embodiments of the device)
20 firing chamber vent
21 cover, vent
22 housing for parts 7-21
23 guide for contact pin
24 combustion chamber
25 particle application

The invention claimed is:

1. A needleless injection device comprising a skin-side membrane (15), wherein the skin-side membrane (15) is provided with a particle application (25), wherein one or more or at least some of the particles is/are larger than the rest of the particles, wherein at least the smaller particles consist of an active agent or contain an active agent, and the larger particles do not contain an active agent.

2. The needleless injection device according to claim 1, wherein one or more or at least some of the particles is/are 2 times, 5 times, 10 times, or 20 times larger than the rest of the particles.

3. The needleless injection device according to claim 1, wherein the proportion of larger particles in the totality of the particle application (25) is 1%, 5%, 10% and more.

4. The needleless injection device according to claim 1, wherein at least the larger particles consist of a pharmaceutically compatible material.

5. The needleless injection device according to claim 1, comprising a chamber (11) containing a pyrotechnic material, wherein the chamber (11) has at least the skin-side membrane (15) at a discharge opening and the skin-side membrane leads into the chamber (11) and the combustion chamber (24) thereof.

6. The needleless injection device according to claim 1, wherein the skin-side membrane (15) has a thickness of from 0.1 mm to 0.6 mm.

7. The needleless injection device according to claim 1, wherein the skin-side membrane (15) consists of steel, titanium, or sheet titanium.

8. The needleless injection device according to claim 1, containing an attachment (17) and/or support disc (16), characterised in that a distance of at least 5 mm is achieved between the skin (18) and the skin-side membrane (15).

9. The needleless injection device according to claim 1, wherein the skin-side membrane is part of a multi-layered or double membrane, consisting of an inner membrane (13) and the skin-side membrane (15).

10. The needleless injection device, wherein at least one of the inner membrane (13) or the skin-side membrane (15) is curved.

11. The needleless injection device according to claim 1, wherein an activation unit (1, 2, 3, 4, 5, 6, 7, 8, 9, 10) is provided in an axial direction relative to the skin-side membrane (15).

12. The needleless injection device according to claim 1 for use of an agent or of an active agent or drug for needle-free application.

* * * * *